US007211264B2

(12) United States Patent
Feldman et al.

(10) Patent No.: US 7,211,264 B2
(45) Date of Patent: *May 1, 2007

(54) ATTENUATED MICROORGANISMS FOR THE TREATMENT OF INFECTION

(75) Inventors: Robert Graham Feldman, Berkshire (GB); Gordon Dougan, Berkshire (GB); Joseph David Santangelo, Berkshire (GB); David William Holden, Berkshire (GB); Jacqueline Elizabeth Shea, Berkshire (GB); Zoe Hindle, Berkshire (GB)

(73) Assignee: Emergent Product Development UK Limited (GB)

( * ) Notice: Subject to any disclaimer, the term of this patent is extended or adjusted under 35 U.S.C. 154(b) by 25 days.

This patent is subject to a terminal disclaimer.

(21) Appl. No.: 10/822,053

(22) Filed: Apr. 8, 2004

(65) Prior Publication Data

US 2004/0191866 A1  Sep. 30, 2004

Related U.S. Application Data

(63) Continuation of application No. 09/569,601, filed on May 9, 2000, now Pat. No. 6,756,042.

(30) Foreign Application Priority Data

May 10, 1999  (GB) .................................. 9910812.8

(51) Int. Cl.
*A01N 63/00* (2006.01)
*A61K 39/112* (2006.01)
*C12N 1/12* (2006.01)

(52) U.S. Cl. ................ 424/258.1; 424/93.1; 435/252.1
(58) Field of Classification Search ............. 424/258.1, 424/93.1; 435/252.1
See application file for complete search history.

(56) References Cited

U.S. PATENT DOCUMENTS

| 5,643,579 | A | 7/1997 | Hung et al. |
| 5,876,931 | A | 3/1999 | Holden |
| 6,756,042 | B1 * | 6/2004 | Feldman et al. ......... 424/258.1 |

FOREIGN PATENT DOCUMENTS

| EP | 0889120 B1 | 1/1999 |
| WO | WO 00/14240 | 3/2000 |

OTHER PUBLICATIONS

Medina, E. et al. "Pathogenicity Island 2 Mutants of *Salmonella typhimurium* Are Efficient Carriers for Heterologous Antigens and Enable Modulation of Immune Responses", *Infection and Immunity*, 1999, pp. 1093-1099, vol. 67, No. 3.

Valentine, P.J. et al. "Identification of Three Highly Attenuated *Salmonella typhimurium* Mutants That Are More Immunogenic and Protective in Mice than a Prototypical aroA Mutant", *Infection and Immunity*, 1998, pp. 3378-3383, vol. 66, No. 7.
Hensel, M. et al. "Genes Encoding Putative Effector Proteins of the Type III Secretion System of *Salmonella* Pathogenicity Island 2 are Required for Bacterial Virulence and Proliferation in Macrophages", *Molecular Microbiology*, 1998, pp. 163-174, vol. 30, No. 1.
Hensel, M. et al. "Analysis of the Boundaries of *Salmonella* Pathogenicity Island 2 and the Corresponding Chromosomal Region of *Escherichia coli* K-12", *Journal of Bacteriology*, 1997, pp. 1105-1111, vol. 179, No. 4.
Hensel, M. et al. "Functional Analysis of ssaJ and ssaK/U Operon, 13 Genes Encoding Components of the Type III Secretion Apparatus of *Salmonella* Pathogenicity Island 2", *Molecular Microbiology*, 1997, pp. 155-167, vol. 24, No. 1.
Shea, J.E. et al. "Influence of the *Salmonella typhimurium* Pathogenicity Island 2 Type III Secretion System on Bacterial Growth in the Mouse", *Infection and Immunity*, 1999, pp. 213-219, vol. 67, No. 1.
Shea, J.E. et al. "Identification of a Virulence Locus Encoding a Second Type III Secretion System in *Salmonella typhimurium*", *Proc. Natl. Acad. Sci. USA*, 1996, pp. 2593-2597, vol. 93.
Chatfield, S. N. et al. "Construction of a Genetically Defined *Salmonella typhi* Ty2 aroA, aroC Mutant for the Engineering of a Candidate Oral Typhoid-Tetanus Vaccine", *Vaccine*, 1992, pp. 53-60, vol. 10, No. 1.
Levine, M.M. et al. "Attentuated *Salmonella* as Live Oral Vaccines Against Typhoid Fever and as Live Vectors", *Journal of Biotechnology*, 1996, pp. 193-196, vol. 44, No. 1-3.
Dougan, G. et al. "Live Bacterial Vaccines and Their Application as Carriers for Foreign Antigene", *Advances in Veterinary Science and Comparative Medicine*, 1989, pp. 277-300, vol. 33.
Hohmann, E.L. et al. "Evaluation of a phoPlphoQ-deleted, aroA-deleted Live Oral *Salmonella typhi* Vaccine Strain in Human Volunteers", *Vaccine*, 1996, pp. 19-24, vol. 14, No. 1.
Lowe, D.C. et al. "Characterization of Candidate Live Oral *Salmonella typhi* Vaccine Strains Harboring Defined Mutations in aroA, aroC, and htrA", *Infection and Immunity*, 1999, pp. 700-707, vol. 67, No. 2.
Schodel, F. et al. "Hepatitus B Virus Nucleocapsid/pre-S2 Fusion Proteins Expressed in Attenuated *Salmonella* for Oral Vaccination", *Journal of Immunology*, 1990, pp. 4317-4321, vol. 145, No. 12.
Plotkin, S. A. *Vaccines*, 1988, p. 571, W.B. Saunders Co., Philadelphia.

* cited by examiner

*Primary Examiner*—Mark Navarro
(74) *Attorney, Agent, or Firm*—Saliwanchik, Lloyd & Saliwanchik

(57) ABSTRACT

The present invention pertains to a *Salmonella* microorganism having an attenuating mutation which disrupts the expression of a gene located within the Spi2 pathogenicity island, and an auxotrophic mutation. The microorganism therefore has a double mutation which helps prevent reactivity of the microorganism while maintaining the effectiveness of the microorganism to elicit an immune response. The present invention also pertains to vaccine compositions and methods for treating and preventing a *Salmonella* infection in a patient.

10 Claims, No Drawings

ATTENUATED MICROORGANISMS FOR THE TREATMENT OF INFECTION

CROSS-REFERENCE TO RELATED APPLICATION

This application is a continuation of U.S. application Ser. No. 09/569,601, filed May 9, 2000, now U.S. Pat. No. 6,756,042.

FIELD OF THE INVENTION

This invention relates to attenuated microorganisms that can be used in vaccine compositions for the prevention or treatment of bacterial or viral infections.

BACKGROUND TO THE INVENTION

It is well established that live attenuated micro-organisms are highly effective vaccines; immune responses elicited by such vaccines are often of greater magnitude and of longer duration than those produced by non-replicating immunogens. One explanation for this may be that live attenuated strains establish limited infections in the host and mimic the early stages of natural infection. In addition, unlike killed preparations, live vaccines are able to induce potent cell-mediated responses which may be connected with their ability to replicate in antigen-presenting cells, such as macrophages.

There has been a long history of the use of live attenuated *Salmonella* vaccines as safe and effective vaccines for the prevention of salmonellosis in animals and humans. Indeed, the live attenuated oral typhoid vaccine. Ty21a (Vivotif), manufactured by the Swiss Serum Vaccine Institute, has proved to be a very successful vaccine for the prevention of typhoid fever and has been licensed in many countries including the US and Europe.

However, the attenuation of this strain was achieved using chemical mutagenesis techniques and the basis of attenuation of the strain is not fully understood. Because of this, the vaccine is not ideal in terms of the number of doses (currently four) and the number of live organisms that have to be given at each dose.

Modern molecular biology techniques coupled with the increasing knowledge of *Salmonella* pathogenesis, has led to the identification of several genes that are essential for the in vivo growth and survival of the organisms. This has provided new gene targets for attenuation leading to the concept that future vaccine strains can be 'rationally' attenuated by introducing defined non-reverting mutations into selected genes known to be involved in virulence. This will facilitate the development of improved vaccines, particularly in terms of the immunogenicity and therefore the number of doses that have to be given.

Although many attenuated strains of *Salmonella* are now known, few have qualified as potential vaccine candidates for use in humans. This may be due in part to the need to balance the immunogenicity of the vaccine with the possibility of the *Salmonella* microorganism becoming reactive It is clear that the selection of appropriate targets for attenuation which will result in a suitable vaccine candidate is not straightforward and cannot easily be predicted. Many factors may influence the suitability of the attenuated strain as an appropriate vaccine, and there is much research being carried out to identify suitable strains. For examples many attenuate strains tested as vaccine candidates lead to vaccinemia or abscesses in the patient.

It is therefore desirable to develop a vaccine having a high degree of immunogenicity with reduced possibility of the microorganism strain reverting to an reactive form and which exhibits a good safety profile with limited side effects.

SUMMARY OF THE INVENTION

The present invention is based on the finding that two specific attenuating mutations introduced into a *Salmonella* microorganism can produce a vaccine having a high degree of immunogenicity and a low risk of the microorganism reverting to a reactive form. The resulting vaccine strains exhibit a good side-effect profile.

The first mutation is contained within a region of the *Salmonella* pathogenicity island two (Spi2), the second is an auxotrophic mutation, i.e. a mutation to disrupt the expression of a gene that encodes a protein required in a biosynthetic pathway.

According to a first aspect of the invention, a *Salmonella* microorganism as an attenuating mutation which disrupts the expression of a gene located within the Spi2 pathogenicity island, and an independent auxotrophic mutation. The preferred attenuating mutation is within the apparatus gene ssaV, and the preferred auxotrophic mutation is within aroC.

The microorganism preferably further comprises one or more heterologous antigens or therapeutic proteins, for example antigens for pathogenic *E. coli, Shigelia* hepatitis A, B or C. Herpes Simplex virus and Human papilloma virus. Therefore, the microorganism may act as a delivery vehicle to immunise against infections other than *Salmonella*.

The *Salmonella* microorganisms may be used to manufacture a vaccine composition which may be administered to a patient via the intravenous or oral route, in a method for the treatment of a bacterial or viral infection, e.g. for the treatment of typhoid.

The attenuated *Salmonella* microorganisms of the present invention form vaccines which surprisingly stimulate mucosal as well as systemic immunity. Further the microorganisms do not cause spleen abscesses in an animal model, whereas mutants with single mutations do. This is a particular advantage of the double mutants as defined herein.

DESCRIPTION OF THE INVENTION

The microorganisms and vaccine compositions of the present invention may be prepared by known techniques.

The choice of particular *Salmonella* microorganism and tree selection of the appropriate mutation, can be mace by the skilled person without undue experimentation. A preferred microorganism is *Salmonella* typhimurium.

A first mutation may be introduced into a gene located within the region of the *Salmonella* pathogenicity island 2, this region being disclosed in WO-A-9617951.

The *Salmonella* pathogenicity island two (Spi2) is one of two classical pathogenicity islands located on the *Salmonella* chromosome. Spi2 comprises several genes that encode a type III secretion system involved in transporting Spi2 encoded virulence-associated proteins (so-called effector proteins) outside of the *Salmonella* bacteria and potentially directly into target host cells such as macrophages. Part of Spi2 (the apparatus genes) encodes the secretion apparatus of the type III system. Spi2 is absolutely essential for the pathogenesis and virulence or *Salmonella* in the mouse, an observation now documented by several different groups around the world. *S. typhimurium* Spi2 mutants are highly attenuated in mice challenged by the oral, intravenous and intraperitoneal routes of administration.

The Spi2 gene may be either an apparatus gene or an effector gene. Preferably, the gene is an apparatus gene. The apparatus genes located within Spi2 are now well characterised; see for example Hensel at al, Molecular Microbiology (1997); 24(1): 155–167 Genes suitable for use in the present invention include ssaV. ssaJ, ssaK, ssaL, ssaM, ssaO, ssaP, ssaQ, ssaR, ssaS, ssaT, ssaU and ssaH genes.

The mutation in the Spi2 region does not necessarily have to be within a gene to disrupt the function. For example, a mutation in an upstream regulatory region may also disrupt gene expression leading to attenuation. Mutations in an intergenic region may also be sufficient to disrupt gene function.

In a preferred embodiment of the invention, the apparatus gene is ssaV in a separate preferred embodiment, the mutation lies within an intergenic region between ssaJ and ssaK The second mutation is termed an "auxotrophic mutation" as it disrupts a gene which is essential in a biosynthetic pathway. The biosynthetic pathway is one present in Salmonella, but not present in mammals. Therefore the mutants cannot depend on metabolites found in the treated patient to circumvent the effect of the mutation. Suitable genes for the auxotrophic mutation, include any aro gene, e.g. aroA, aroC, aroD and aroE.

In a preferred embodiment of the invention, the vaccine composition comprises a Salmonella microorganism raving attenuating mutations in ssaV and aroC.

The mutations may be introduced into the microorganism using any known technique. Preferably, the mutation is a deletion mutation, where disruption of the gene is caused by the excision of nucleic acids. Alternatively, mutations may be introduced by the insertion of nucleic acids or by point mutations. Methods for introducing the mutations into the specific regions will be apparent to the skilled person.

In addition to the two mutations, the Salmonella microorganism may also comprise heterologous antigens. The attenuated microorganism can therefore act as a delivery vehicle for administering antigens against other bacterial or viral infections. Antigens which are suitable for use in this way will be apparent to the skilled person and include:

Pathogenic E. coli antigens, i.e. ETEC
Hepatitis A, B and C antigens
Lime disease antigens
vibrio cholera antigens
Helicobacter antigens
Herpes Siimplex virus antigens
Human papilloma virus antigens This system also has the potential to deliver therapeutic proteins, e.g. cytokines, for the treatment of patients, e.g. patients infected with hepatitis. Methods for the delivery of heterologous antigens or therapeutic proteins using the vaccine compositions will be apparent to the skilled person.

Vaccines made using the microorganisms of the invention have application to the treatment of infections in human patients and in the treatment of veterinary infections.

The double mutation provides an effective means to attenuate the microorganism to provide a safe vaccine candidate.

The vaccine compositions provide effective protection even in immunocompromised patients, and importantly offer a low risk in developing spleen abscesses. Spleen abscesses have been identified using vaccines based on a single mutation, and therefore the present compositions may offer a substantial benefit to patients.

To formulate the vaccine compositions, the mutant microorganisms may me present in a composition together with any suitable pharmaceutically acceptable adjuvant, diluent or excipient. Suitable formulations will be apparent to the skilled person. The formulations may be developed for any suitable means of administration. Preferred administration is via the oral or intravenous routes and the vaccines are live attenuated Salmonella microorganisms. The number of microorganisms that are required to be present in the formulations can be determined and optimised by the skilled person. However, in general, a patient may be administered approximately $10^{7-10^{10}}$ CFLs, preferably approximately $10^{4-10^{9}}$ CFUs in a single dosage unit.

The following Examples illustrate the invention

EXAMPLE 1

This Example describes the preparation of a mutant strain designated ZH9 which has activity as a human oral typhoid vaccine. The strain is derived from the virulent S. typhi strain Ty2, originally isolated from a case of typhoid. The derived strain has a defined mutation within purA and aroA.

Ty2 for the Construction of ZH9

S. typhi Ty2 was originally isolated from an individual with typhoid fever in 1916 and has been used for the derivation of all licensed typhoid vaccines. The strain was obtained from the PHLS national culture collection at Colindale. It was obtained as a lyophilised culture, the NCTC number being 8385.

Cloning the S. typhi aroC gene from S. typhi Ty2

S. typhi Ty2 was recovered from stock and grown overnight in Luna Bertani (LB) broth. The cells were harvested and whole cell DNA was prepared. DNA fragments of S. typhi Ty2 DNA were generated by partial cleavage with the restriction enzyme Sau3A and the resulting fragments were ligated to BamI11 cleaved pHC79 to generate a cosmid library of S. typhi Ty2 DNA using E. coli HU835 as recipient. To isolate the DNA encoding aroC from the S. typhi DNA the cosmid library was used to transduce E. coli AB2849 which harbours a mutation in the aroC gene and is dependant on aromatic compounds for grown. The transduction mixture was plated onto minimal medium lacking aromatic compounds and incubated at 37° C. A number of isolated colonies were observed following overnight incubation. These bacteria had presumably arisen as a consequence of complementation of the aroC mutation in AB2849 by a cosmic clone harbouring the intact aroC gene from. Cosmid DNA from one of these strains was purified. A 5.2 kb HindIII fragment from this cosmic was cloned into pUC18 to give plasmid pTAC2 which was able to complement the deletion of aroC in AB2849, demonstrating that it contains the S. typhi aroC gene Generation of a Defined Deletion of the Cloned S. typhi Ty2 aroC A defined 600 bp deletion was created within the cloned aroC gene using PCR. The oligonucleotide primers used in the PCR were designed using the published DNA sequence of the S. typhi aroC gene (Acc. M27715). The DNA 5' to the aroC gene was amplified from pTAC2 using primers SEQ ID NO. 3 and SEQ ID NO. 1. SEC ID NO 3 anneals to vector DNA. SEQ ID NO. 1 anneals to the 5' region of aroC. The DNA 3' to the aroC gene was amplified using primers SEQ ID NO. 4 and SEC ID NO: 2 SEQ ID NO. 4 anneals to vector DNA. SEQ ID NO. 2 anneals to the 3' region of aroC. The resulting PCR products had XbaI sites incorporated into the 5' ends to facilitate cloning. The fragments were cloned into the vector pUC18 The final plasmid construct designated pMIAC23 contains a defined deletion of aroC (position 544 to 1143) on a 4.8 kb HindIII fragment. The HindIII fragment is inserted at the HindIII site of pUC18. A single XbaI site is present at the site of the aroC deletion.

Introduction of the aroC Mutation into the *S. typhi* Ty2 Genome

The suicide plasmid pCVD442 (Donnenberg & Kaper, Infection and immunity, 1991; 59: 4310–4317) was uses as a vector to introduce the aroC deletion into the genome of *S. typhi* Ty2. The 4.8 kb HindIII fragment containing the aroC deletion was isolated from pMIAC23 and the ends made blunt by using the Stratagene DNA polishing kit. Plasmid pCVD442 was linearized by digestion wit SmaI treated with alkaline phosphatase and ligated to the blunt-ended fragments. The required construct was isolated and denoted pYCVC21.

pYCVC21 was introduced into *S. typhi* Ty2 by using a standard electroporation protocol. The plasmid was able to integrate into the Ty2 genome following recombination between the homologous regions on the plasmid and the genome to give ampicillin resistant transformants. These transformants contained a copy of both the original wild type aroC and the deleted aroC gene. Growing these strains in the absence of ampicillin allowed for a second recombination event to occur which resulted in loss of the pCVD442 DNA sequences and one copy of the aroC gene, either the wild-type copy or the deleted copy. *S. typhi* Ty2 bacteria which had undergone this second recombination event were identified as ampicillin sensitive derivatives which were able to grow in the presence of 5% sucrose (pCV442 carries the sacB gene which when expressed results in a sucrose sensitive phenotype). Strains that had retained only the deleted aroC gene were initially identified as strains that were unable to grow on minimal media plates in the absence of a supplement of aromatic compounds The aroC genotype was confirmed by using PCR analysis Primers having SEQ ID NO. 5 and SEQ ID NO. 6 gave a product of 994 bp for the wild type aroC and 400 bp for the deleted aroC gene. Sequence analysis of the resulting PCR products confirmed the presence of the required deletion in 6 individual isolates designated DTY6, DTY7, DTY8, DTY9 and DTY10. These strains were stored in Microbank vials at −70° C. for long term storage. Strain DTY8 was chosed for further manipulation.

Introduction of an ssaV Mutation into the *S. typhi* aroC Mutant DTY8

A 7.5 kb PstI fragment containing the ssaV region of *S. typhi* was amplified from a total DNA preparation by using PCR and cloned into the vector pCR21 (Invitrogen). The PCR oligonucleotide primers employed having SEQ ID NO. 7 and SEQ ID NO. 8, were designed to the *S. typhimurium* SPI2 sequence. The resulting plasmid construct was designated pTYSV21.

A plasmid construct possessing a deletion of the ssaV gene was derived from pTYSV21 by using reverse orientation PCR. Primers annealing to the 5' (SEQ ID NO. 9) and 3' (SEQ ID NO. 10) regions of the ssaV open reading frame were designed to the *S. typhimurium* Spi2 sequence. An AvtII restriction site was incorporated into me region of each primer an XbaI site was incorporated into SEQ ID NO. 10. The XbaI site serves as a tag for the ssaV mutation so it can be detected easily by restriction analysis. The resulting PCR produce was subjected to digestion with AvtII and the backbone plasmid molecules purified following agarose gel electrophoresis Recircularisation of the resulting fragments at the AvtII sticky-ends gave the required deletion construct pYDSV1. pYDSV1 contains a 5.5kb PstI fragment with a defined 1894 bp deletion within the ssaV open reading frame.

The suicide plasmid pCVD442 was used as a vector to introduce the ssaV deletion into the genome of the *S. typhi* Ty2 aroC mutant DTY8. The 5.5 kb PstI fragment containing the ssaV deletion was isolated from pYDSV1 and the ends made blunt by treatment with Klenow DNA polymerase. Plasmid pCVD442 was linearized by digestion with SmaI, treated with alkaline phosphatase and ligated to yhe blunt-ended fragments. The required construct was isolated and denoted pYDSV214.

pYDSV214 was introduced into *S. typhi* DTY8 by using electroporation. Ampicillin-resistant transformants were selected and then grown in the absence of ampicillin to allow for loss of the pCVD442 DNA sequences and one copy of the ssaV gene either the wild-type copy or the deleted copy. Strains that had undergone this second recombination event were identified as ampicillin-sensitive sucrose-resistant colonies. Strains that had retained only the deleted ssaV gene were identified by using PCR analysis. Primers having SEQ ID NO. 11 and SEQ ID NO. 12 gave a product of 2485 bp for the wild type ssaV and 591 bp for the deleted ssaV gene. Sequence analysis of the resulting PCR products confirmed the presence of the required deletion in 5 individual isolates, ZH2, ZH4, ZH6, VH7 and SVH9. Strain ZH9 was chosen for manufacture of a CGMP master call bank.

EXAMPLE 2

This Example describes the preparation of a *S. typnimurium* mutant strain designated WT05 which has vaccine activity against human gastroenteritis. The strain is derived from the known human virulent *S. typhimurium* strain TML.

TML for the Construction of WT05.

TML was originally isolated from a patient suffering from gastroenteritis and was identified in the laboratories of Dr John Stevens at Birmingham University. It was lyophilised at Welcome Research Laboratories and assigned a culture number BRD 519. The culture was obtained from Birmingham University.

Generation of a defined deletion of the cloned *S. typhimurium* ssaV gene

A plasmid (Plasmid 7-2. Shea et al. PNAS, 1996; 93: 2593–2597) was generated by cloning a 7.5 kb PstI fragment isolated from *S. typhimurium* LT2 into the PstI site of pUC18. ssaV is positioned centrally on this fragment A plasmid construct containing a defined deletion of the ssaV ORF was derived from plasmid 7-2 by using reverse orientation PCR. Primers annealing to the 5' (SEQ ID NO. 13) and 3' (SEQ ID NO. 14) regions of the ssaV open reading frame were designed to the *S. typhimurium* Spi2 sequence. An AvtI restriction site was incorporated into the 5' region of each primer and an XbaI site was incorporated into SEQ ID NO. 14. The XbaI site serves as a tag for the ssaV mutation so it can be detected easily by restriction analysis. The resulting PCR product was subjected to digestion with AvrtI and the backbone plasmid molecules purified following agarose gel electrophoresis. Re-circularisation of the resulting fragments at the AvtII sticky-ends gave the required deletion construct designated pMDSV1. pMDSV1 contains a 5.5 kb PstI fragment with a defined 1894 bp deletion within the ssaV open reading frame, an AvtI and a XbaI restriction site are at the site of the deletion.

The suicide plasmid pCVD442 was used as a vector to introduce the ssaV deletion into the genome of *S. typhimurium* TML. The 5.5 kb PstI fragment containing the ssaV deletion was isolated from pMDSV1 and the ends made blunt by treatment with Klenow DNA polymerase. Plasmid pCVD442 was linearized by digestion with SmaI treated with alkaline phosphatase and ligated to the blunt-ended fragments. The required construct was isolated and denoted pMDSV22.

pMDSV22 was introduced into *S. typhimurium* TML using conjugation. To this end the construct was transformed into the *E. coli* strains S17-1 λ par. The conjugation was performed according to standard procedures. Plasmid pMCSV22 was able to integrate into the TML genome following recombination between the homologous regions on the plasmid and the genome to give ampicillin resistant transconjugants. A transconjugate designated masv-WT2 was chosen for further manipulations. This transconjugant contains a copy of both the original wild-type ssaV and the deleted ssaV gene. It was grown in the absence of ampicillin to allow for a second recombination event to occur which would result in the loss of the pCVD442 DNA sequences and one copy of the ssaV gene either the wild-type copy or the deleted copy. Isolates which had undergone this second recombination event were identified as ampicillin-sensitive derivatives which were able to grow in the presence of 5% sucrose (pCVD442 carries the sacB gene which when expressed results in a sucrose-sensitive phenotype). Strains that had retained only the deleted ssaV gene were identified by using PCR analysis. Primers having SEQ ID NO. 15 and SEQ ID NO. 16 gave a product of 2485 bp for the wild type ssaV and 591 bp for the deleted ssaV gene Sequence analysis of the resulting PCR products confirmed the presence of the required deletion in 4 individual isolates, ZH20, ZH23, ZH25 and ZH26. These strains were stored in LB plus 15% glycrol at −80° C. for long-term storage. Strain ZH26 was chosen for further manipulation.

Cloning the *S. typhimurium* aroC gene from *S. typhimurium* TML

Genomic DNA was isolated from *S. typhimurium* TML and cleaved with HindIII. HindIII fragments in the size range 5 to 6 kb were purified and ligated to HindIII-cleaved pBluescript. The ligation mixture was used to transform an *E. coli* aroC mutant, AB2849 and clones containing the *S. typhimurium* aroC gene were selectee by virtue of their ability to complement this strain. Analysis of one clone pDAC1, demonstrated that it contained a 5.2 kb HindIII fragment A defined 600 bp deletion was created within the cloned aroC gene by using PCR. The oligonucleotide primers were designed using the published DNA sequence of the *S. typhi* aroC gene (Acc M27715). The DNA 5' to the aroC gene was amplified from pDAC1 using primers having SEQ ID NO. 19 and SEQ ID NO. 17. SEQ ID NO 19 anneals to vector DNA, SEQ ID NO. 17 anneals to the 5' region of aroC. The DNA 3' to the aroC gene was amplified using primers having SEQ ID NO. 20 and SEQ ID NO. 18. SEQ ID NO. 20 anneals to vector DNA, SEQ ID NO. 18 anneals to the 3' region of aroC. The resulting PCR products had XbaI sites incorporated into the 5' ends to facilitate cloning. The fragments were cloned into the vector pUC18. The final plasmid construct pMIAC3 contains a defined deletion of aroC (Acc. M27715 position 544 to 1143) on a 4.8 kb HindIII fragment. The HindIII fragment is inserted at the HindIII site of puC18. A single XbaI site is present at the site of the deletion.

Introduction of the aroC mutation into the *S. typhimurium* ssaV mutant ZH26

The suicide plasmid pCVD442 was used as the vector to introduce the aroC deletion into the genome of *S. typhimurium* TML. The 4.8 kb HindIII fragment containing the aroC deletion was isolated from pMIAC8 and the ends made blunt by using the Stratagene DNA polishing Kit (Part No. 200409). Plasmid pCVD442 was linearized by digestion with SmaI treated with alkaline phosphatase and ligated to the blunt-ended fragments. The required construct was isolated and denoted pMCVC16 pMCVC16 was introduced into *S. typhimurium* ZH26 by using electroporation. Ampicillin-resistant transformants were selected and allowed to crow in the absence of ampicillin to allow for loss of the pCVD442 DNA sequences and one copy of the aroC gene, either the wild-type copy or the deleted copy. Strains that had undergone this second recombination event were identified as ampicillin-sensitive derivatives that were able to grow in the presence of 5% sucrose. Strains that had retained only the deleted aroC gene were initially identified as strains that were unable to grow on minimal media plates in the absence of a supplement of aromatic compounds. The aroC genotype was confirmed by using PCR analysis. Primers having SEQ ID NO. 21 and SEQ ID NO. 22 give a product of 994 bp for the wild type aroC and 400 bp for the deleted aroC gene. Sequence analysis of the resulting PCR products confirmed the presence of the required deletion in 4 individual isolates designated WT05, WT09. WT10 and WT12. Strain WT05 was chosen for manufacture of a CGMP master cell bank.

EXAMPLE 3

The following construct was prepared to test the double mutant vaccines in an animal model. *S. typhimurium* SL1344, a strain that infects mice was used with single and double mutations present.

An ssaV:apn (non-polar) mutation from *S. typhimurium*. 12023s was P22 transduced to SL1344 to give the single Spi2 mutant.

The aroC deletion/pCVD422 suicide vector pMCVC16 was electroporated into the *S. typhimurium* strain LB5010 and merodiploids were obtained. The aroC deletion merodiploid was then P22 transduced from the LB5010 merodiploid to SL1344. The SL1344 merodiploid was then resolved using sucrose selection to give the single aroC mutant.

The double mutant was generated by P22 transduction of the aroC deletion merodiploid from LB5010 into the SL1344 ssaV::aph. Plasmid sequences were resolved from the merodiploid leaving strain 3, the aroC deletion mutation in the ES1344 ssaV::aph background.

Pre-Clinical Pharmacodynamic Studies on Defined aaro-ClssaV *Salmonella* Mutants

*Salmonella* mutants (strain SL1344) harbouring defined mutations in either aroC. ssaV or a combination of both mutations have been evaluated extensively in BALB/C mice to assess attenuation persistence of the organisms and ability to immunise against challenge with the wild type strain.

EXAMPLE 4

Animals Immunised by the Intravenous Route

Protection studies

Groups of ten BALB/C mice were immunised i.v. with $10^5$ and $10^6$ organisms of SL1344 aroC, SL1344 ssaV, and SL1344 aroC. ssaV grown overnight in L3 broth and resuspended in saline for administration. Mice were challenged 6 weeks later with $10^5$ wild type organisms given intravenously. Ten organisms of this wild type strain given intravenously are sufficient to kill mice.

All the mice given the single aroC or ssaV mutants were solidly protected after challenge with either dose and remained well throughout the experiment, exhibiting no sign of disease. For the double mutant 90% of the animals were solidly protected that received the immunisation with $10^8$ organisms. One of the animals died 8 days after the challenge. For the animals that were immunised with the lower dose, only 1 of the mice survived the challenge.

This experiment demonstrates that immunisation with *Salmonella* ssaV mutants, either alone, or in combination with an aroC mutation will immunise mice against challenge with the wild type *Salmonella* strain.

Persistence of Strains

Groups of mice were given $10^6$ organisms of the three *Salmonella* mutants described above. Four mice were sacrificed at different time points up to day 14 and enumeration of organisms in livers and spleens were performed. Counts of all three mutants were comparable up until day 10 when the counts were approximately $5 \times 10^5$ organisms in each organ. At day 14 a difference was demonstrated between the single mutants and the double mutants, there being a log less in the numbers of a double mutant organisms in both liver and spleens.

The other important difference between the single mutant and the aroC/ssaV double mutant is that there were no liver abscesses present at any time during the experiment for the double mutants. However the mice infected with the single mutants did have liver abscesses present at day 10 and 14. This is an important finding and strongly supports the use of this combination of mutations for evaluation the preparation of vaccines.

Immunogenicity

Mice immunised as above were bled and the antibody titres were determined against whole cell *Salmonella* using an ELISA. All three strains were demonstrated to be highly immunogenic, eliciting high titres of circulating IgG against *Salmonella*.

EXAMPLE 5

Animals Immunised by the Oral Route

Persistence of Strains

Groups of mice immunised orally with $5 \times 10^6$ organisms of each of the three *Salmonella* mutants were sacrificed at periodic intervals and the numbers of organisms enumerated in livers and spleens. For the single aro mutant and the single ssaV mutant counts in livers and spleens were $10^3$ and $10^2$ respectively up until about day 21. Thereafter the numbers reduced. For the mice that received the aroC. ssaV double mutants, organisms were virtually undetectable in the livers and spleens after oral immunisation.

Oral Immunisation and Intravenous Challenge of A–J Mice Vaccinated with *Salmonella typhimurium* TML aroC/ssaV (WT05).

The purpose of this experiment was to ascertain the protective efficacy of $5 \times 10^9$ aroC/ssaV *S. typhimurium* TML mutants in an oral ity[1] murine vaccination and intravenous challenge model. This model more closely resembles the human response to *Salmonella* in that these animals are less susceptible than an ity[2] background.

$5 \times 10^5$ *S. typhimurium* TML aroC/ssaV in a volume or 0.2 ml PBS was inoculated orally by gavage tube into 10 6–8 week old. A–J mice and left 8 weeks. Two mice were given PBS only at this time and served as control animals. After 8 weeks had elapsed the two immunised groups were challenged intravenously with $10^7$ wild type *S. typhimurium* TML. Mice were observed for 30 days post challenge.

All animals were solidly protected against wild type challenge (100% survival. 10/10 animals alive). Mice given PBS alone and then challenged with wild type *S. typhimurium* TML died on day 6 post challenge In an ity[1] background the double *S. typhimurium* ML aroC/ssaV seems to protect mice given an oral dose of $5 \times 10^6$. This may be important for the human situation as ity[2] mice are a better model of human salmonellosis, in terms of susceptibility to infection.

Studies were also carried out to evaluate the persistence of the double mutants in the livers and spleens of the mice. It was found that the double mutants persist at low levels to around day 21. By day 28, the mutant strain has been cleared.

EXAMPLE 6

Human Clinical Trial 18 healthy volunteers were recruited to an open label, non-placebo controlled study. Following appropriate screening, each of 3 volunteers received a single oral dose of either $10^7$, $10^8$ or $10^9$ CFUs of *S. typhi* ZH9 or *S. typhimurium* WT05. The microorganisms prepared as above were resuspended to the appropriate dosing concentrations in a final volume of 100 ml of 2% (w/v) sodium bicarbonate solution to neutralize gastric acid. This liquid suspension was administered orally to the volunteers. The volunteers were then isolated for 72 hours, and then followed up post immunisation for safety and immunogenicity.

Volunteers were assessed for reactogenicity and other adverse events associated with vaccination by observation, physical examination and by the completion of diary cards. In addition, blood, stool and urine cultures were collected to assay for vaccinaemia, shedding and persistence of the vaccine strains. Additional safety data was obtained by measuring levels of C-reactive protein (CRP) and liver function enzymes (ALT) in blood, total white blood cell (WBC) counts and erythrocyte sedimentation rates (ESR) using standard procedures. These parameters were measured on blood taken daily until day 7 and then at weekly intervals until day 28.

Analysis of Mucosal and Systemic Immune Responses

Blood and saliva samples were collected prior to immunization and then on days 7, 14, 21 and 28 after immunization, Saliva and serum were frozen at $-70°$ C. until analysis by ELISA. Peripheral blood mononuclear cells were collected and assayed for the presence of antibody-secreting cells (ASCs) using the ELISPOT technique.

Both *S. typhi* ZH9 and *S. typhimurium* WT05 were well aclerated in all of me volunteers. No serious adverse events were noted in any of the volunteers at each of the 3 dose levels and blood and urine cultures remained negative in all vaccines at all time-points examined. Thus, immunisation with both *S. typhi* ZH9 and *S. typhimurium* WT05 do not result in vacinaemias. None of the volunteers given either of the strains developed diarmoea or persistent high-grade fever, further indicating the safety of the vaccine strains. Persistent excretion nor vaccnaemia beyond day 7 was not observed in either of the 3 dose groups of *S. typhi* ZH9 or in the low dose ($10^7$) of *S. typhimurium* WT05.

Mucosal and Systemic Immune Responses Elicited by *S. typhi* ZH9

Oral immunization with a single low dose (1 ×$10^7$ CFUs) of *S. typhi* ZH9 resulted in the priming of *S. typhi*-specific IgA-secreting ASCs in 2 of 3 volunteers detected 7 days after immunization. Subsequence testing on days 14 and 21 showed that IgA ASCs were still detectable but at much lower levels and had disappeared by day 28 in almost all responder vaccinees, numbers of ASCs were highest on day 7. Surprisingly, ingestion of a higher dose ($10^4$ CFUs) of *S. typhi* ZH9 resulted in a low IgA ASC response in only one of three vaccinees. Ingestion of the highest dose (1×$10^8$ CFUs) primed IgA ASCs in 2 of 3 volunteers

*Salmonella*-Specific Serum Antibody Response

Oral immunization with a single low dose (1×$10^7$ CFUs) of *S. typhi* ZH9 failed to elict *S. typhi* LPS-specific serum IgG (despite generating IgA-ASCs in ⅔ vaccinees) when examined on days 7, 14, 21 and 28. Similarly only ⅓ produced very low levels of flagella-specific IgG. However, ingestion of $10^8$ CFUs resulted in the production of high levels of both LPS and flagella-specific IgG in all 3 volunteers. Increased levels of *S. typhi* LPS specific and flagella-specific were detected as early as 7 days after vaccination, rising on cay 14 and remaining high on day 28. The highest dose of $10^9$ CFUs also stimulated LPS- and flagella-specific IgG in 2 of 3 vacinees, detectable on days 7 and 14 respectively.

Conclusions

This study demonstrated the utility of the ssaV mutation, as a component of any new oral typhoid vaccine strain. An *S. typhi* strain harbouring aro mutations alone would have caused vaccinaemias at the doses given. The ssaV mutation therefore provides an additional level of safety to the aro mutation alone by abolishing the vaccinaemias using this early formulation.

As well as proving to be well-tolerated ZH9 was also demonstrated to be immunogenic at all three dose levels given. With regard to stimulating serum antibody, the intermediate ($10^8$ CFUs) and highest ($10^9$ CFUs) doses proved to be highly immunogenic, with 3/3 vaccines given $10^8$ CFUs and ⅔ given $10^9$ CFUs eliciting high titres of both *S. typhi* LPS and flagella specific-serum IgG. These responses are very encouraging since it is generally difficult to elicit serum antibody by oral vaccination.

As well as generating *S. typhi*-specific serum antibody responses, ZH9 also primed IgA ASCs, indicative of immune stimulation at the intestinal mucosa. A total of ⅚volunteers elicited an *S. typhi* LPS-specific IgA-secreting cell (ASC) response which did not appear to be dose-dependent WT05 was also well tolerated and no vaccnaemias were detected. Interestingly, no diarrhoeas or symptoms of gastroenteritis were detected in any of volunteers. The previous data obtained using the mutant TML strain with single aro or SPI 2 mutations in *S. typhimurium* given to mice suggested that a double aroC/ssaV mutant might cause some local intestinal effects e.g. diarrhoea, cramps in humans. The absence of these events further supports the utility of the combination of aro and SPI2 mutations.

EXAMPLE 7

Heterologous Antigen Carriers

To demonstrate the utility of the ssaV:aroC double mutant strains to express and deliver foreign antigens, WT05 was transformed with a plasmid (pBRD026) expressing the gene for the *E. coli* heat-labile entertoxin B subunit (LT-B).

BALB/C mice (n=10/group) were immunised orally on days 0 and 28 with $10^9$ CFUs (200 ml in PBS) WT05 expressing pBRD026, or with the WT05 vector strain (control). For comparison (and as a positive control) a group of mice (n=5) were immunised orally on days 0 and 28 with 10 μg purified LT (Sigma). Negative control mice (n=5) were immunise orally on days 0 and 28 with 200 μl PBS. Mice were bled from the tail vein on days 21, 28, 35 and by cardiac puncture on day 42 and sera and intestinal lavage (day 42 only) collected and stored at −20° C.

All but one of the mice immunised with WT05/LT-B elicited LT-specific IgG (titres of 3,000–50,000) on day 28 after a single oral dose. None of the control mice immunised orally with WT05 or PBS elicited LT-specific IgG. Oral immunisation with a single dose of purified LT elicited higher titres of LT-specific antibody (titres of 6,000–>50, 000). When the isotype of the LT-B-specific serum IgG was examined, it was found that the WT05 strain expressing pBRD026 elicited almost exclusively LT-specific IgG1a, indicating a bias towards a TH1-type immune response. In contrast, mice immunized with purified LT (Sigma) elicited almost exclusively LT-specific IgG1, indicating a TH2-type response. Therefore, expressing the LT-B within the aroC/ssaV strain facilitates profound immune modulation. The TH1-biased responses generated by the *Salmonella* aroC/ssaV strain will be important when antigens from pathogenic organisms for which, TH1-type responses are protective, are expressed.

We claim:

1. An isolated *Salmonella* microorganism having an attenuating mutation which disrupts the expression of an ssaJ apparatus gene located within the Spi2 pathogenicity island, and an auxotrophic mutation which disrupts the expression of an aroC gene.

2. The microorganism according to claim 1, wherein the attenuating mutation is within an intergenic region between ssaK and ssaJ.

3. The microorganism according to claim 1, wherein the microorganism further comprises a heterologous antigen or a therapeutic protein.

4. The microorganism according to claim 3, wherein the antigen is a hepatitis A, B or C antigen.

5. The microorganism according to claim 1, wherein the microorganism is *Salmonella typhi* Ty2.

6. A vaccine composition comprising a microorganism according to claim 1, and an adjuvant and a physiologically acceptable diluent.

7. The vaccine composition according to claim 6, comprising from about $10^7$ to about $10^{10}$ CFUs in a single dosage unit.

8. The vaccine composition according to claim 7, comprising from about $10^8$ to about $10^9$ CFUs in a single dosage unit.

9. A method for treating or preventing a *Salmonella* infection, comprising administering to a patient a microorganism according to claim 1.

10. The method according to claim 9, for the treatment of typhoid.

* * * * *

SEQUENCE LISTING

<160> NUMBER OF SEQ ID NOS: 22

<210> SEQ ID NO 1
<211> LENGTH: 36
<212> TYPE: DNA
<213> ORGANISM: Artificial Sequence -continued

```
<220> FEATURE:
<223> OTHER INFORMATION: Oligonucleotide

<400> SEQUENCE: 1
aatcagtcta gaaatactgg tgccggtcgt cacgcc                    36

<210> SEQ ID NO 2
<211> LENGTH: 36
<212> TYPE: DNA
<213> ORGANISM: Artificial Sequence
<220> FEATURE:
<223> OTHER INFORMATION: Oligonucleotide

<400> SEQUENCE: 2
aatcagtcta gaagtgggca acacattgtg gcgcat                    36

<210> SEQ ID NO 3
<211> LENGTH: 23
<212> TYPE: DNA
<213> ORGANISM: Artificial Sequence
<220> FEATURE:
<223> OTHER INFORMATION: Oligonucleotide

<400> SEQUENCE: 3
cccagtcacg acgttgtaaa acg                                  23

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide

<400> SEQUENCE: 4
agcggataac aatttcacac agg                                  23

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide

<400> SEQUENCE: 5
cggcgaatca cacgggctgg c                                    21

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide

<400> SEQUENCE: 6
ggcgcagcag gtgatccatc a                                    21

<210> SEQ ID NO 7
<211> LENGTH: 35
<212> TYPE: DNA
<213> ORGANISM: Artificial Sequence
<220> FEATURE:
<223> OTHER INFORMATION: Oligonucleotide

<400> SEQUENCE: 7
gccactaaca cgataacggt tgcgtgaaaa ccacg                     35
```

<210> SEQ ID NO 8
<211> LENGTH: 32
<212> TYPE: DNA
<213> ORGANISM: Artificial Sequence
<220> FEATURE:
<223> OTHER INFORMATION: Oligonucleotide

<400> SEQUENCE: 8
tgtaaagtcc tctgcagaac cgagccagga gc          32

<210> SEQ ID NO 9
<211> LENGTH: 61
<212> TYPE: DNA
<213> ORGANISM: Artificial Sequence
<220> FEATURE:
<223> OTHER INFORMATION: Oligonucleotide

<400> SEQUENCE: 9
caccgtccct aggaccatat cctgccgacc cgcgcataca ctgagccact gttgcgccct     60
g                                                                    61

<210> SEQ ID NO 10
<211> LENGTH: 63
<212> TYPE: DNA
<213> ORGANISM: Artificial Sequence
<220> FEATURE:
<223> OTHER INFORMATION: Oligonucleotide

<400> SEQUENCE: 10
ggcaggacct aggctagtct agacttatac aagtggtaga agtattgac cttagcgaag      60 agg                                                                  63

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
aatatgttct ggcggcaagg                                                20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
atccccacga cttcagcaag                                                20

<210> SEQ ID NO 13
<211> LENGTH: 61
<212> TYPE: DNA
<213> ORGANISM: Artificial Sequence
<220> FEATURE:
<223> OTHER INFORMATION: Oligonucleotide

<400> SEQUENCE: 13
caccgtccct aggaccatat cctgccgacc cgcgcataca ctgagccact gttgcgccct     60
g                                                                    61

<210> SEQ ID NO 14
<211> LENGTH: 63
<212> TYPE: DNA
<213> ORGANISM: Artificial Sequence
<220> FEATURE:
<223> OTHER INFORMATION: Oligonucleotide

<400> SEQUENCE: 14
ggcaggacct aggctagtct agacttatac aagtggtaga agtattgac cttagcgaag    60 agg                                                                 63

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide

<400> SEQUENCE: 15
aatatgttct ggcggcaagg                                               20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide

<400> SEQUENCE: 16
atccccacga cttcagcaag                                               20

<210> SEQ ID NO 17
<211> LENGTH: 36
<212> TYPE: DNA
<213> ORGANISM: Artificial Sequence
<220> FEATURE:
<223> OTHER INFORMATION: Oligonucleotide

<400> SEQUENCE: 17
aatcagtcta gaaatactgg tgccggtcgt cacgcc                             36

<210> SEQ ID NO 18
<211> LENGTH: 36
<212> TYPE: DNA
<213> ORGANISM: Artificial Sequence
<220> FEATURE:
<223> OTHER INFORMATION: Oligonucleotide

<400> SEQUENCE: 18
aatcagtcta gaagtgggca acacattgtg gcgcat                             36

<210> SEQ ID NO 19
<211> LENGTH: 23
<212> TYPE: DNA
<213> ORGANISM: Artificial Sequence
<220> FEATURE:
<223> OTHER INFORMATION: Oligonucleotide

<400> SEQUENCE: 19
cccagtcacg acgttgtaaa acg                                           23

<210> SEQ ID NO 20
<211> LENGTH: 23
<212> TYPE: DNA
<213> ORGANISM: Artificial Sequence
<220> FEATURE:

-continued

```
<223> OTHER INFORMATION: Oligonucleotide

<400> SEQUENCE: 20
agcggataac aatttcacac agg                                            23

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide

<400> SEQUENCE: 21
cggcgaatca cacgggctgg c                                              21

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide

<400> SEQUENCE: 22
ggcgcagcag gtgatccatc a                                              21
```